United States Patent
Chaudhury et al.

(10) Patent No.: US 12,419,593 B2
(45) Date of Patent: Sep. 23, 2025

(54) ULTRASONIC HAPTIC SYSTEM FOR PATIENT NUDGING

(71) Applicant: KONINKLIJKE PHILIPS N.V., Eindhoven (NL)

(72) Inventors: Sudipta Chaudhury, Bangalore (IN); Rajendra Singh Sisodia, Bhopal (IN); Mark Thomas Johnson, Arendonk (BE); Michael Günter Helle, Hamburg (DE); Ravindra Bhat, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 860 days.

(21) Appl. No.: 17/413,027

(22) PCT Filed: Dec. 11, 2019

(86) PCT No.: PCT/EP2019/084554
§ 371 (c)(1),
(2) Date: Jun. 11, 2021

(87) PCT Pub. No.: WO2020/120529
PCT Pub. Date: Jun. 18, 2020

(65) Prior Publication Data
US 2022/0015722 A1    Jan. 20, 2022

(30) Foreign Application Priority Data

Dec. 13, 2018  (EP) .................................... 18212245

(51) Int. Cl.
*A61B 5/00*    (2006.01)
*A61B 6/00*    (2006.01)
(Continued)

(52) U.S. Cl.
CPC .................. *A61B 6/04* (2013.01); *A61B 5/70* (2013.01); *A61B 6/032* (2013.01); *A61B 6/037* (2013.01); *A61B 6/467* (2013.01); *A61B 6/548* (2013.01)

(58) Field of Classification Search
CPC ........ G16H 20/40; G16H 30/20; G16H 40/63; A61N 5/107; A61N 2005/1074; A61N 5/1049; A61B 5/704; A61B 6/0407
See application file for complete search history.

(56) References Cited

U.S. PATENT DOCUMENTS 5,899,861 A * 5/1999 Friemel ............... G01S 7/52074
                                                          600/443
9,489,734 B2   11/2016 Gum
(Continued)

FOREIGN PATENT DOCUMENTS

CN      108022641 A    5/2018
JP      2005143891 A   6/2005
(Continued)

OTHER PUBLICATIONS

PCT International Search Report, International application No. PCT/EP2019/084554, Feb. 20, 2020.
(Continued)

*Primary Examiner* — Santosh R Poudel
(74) *Attorney, Agent, or Firm* — Larry Liberchuk

(57) ABSTRACT

A system (PPS) for patient positioning in imaging or radiation therapy. The system comprises a transmitter (TX). The transmitter (TX) is configured to generate an outgoing signal capable of inducing, from a distance, a haptic sensation at an impact region (IRE) on the patient's skin. The system further comprises a control logic (CL) configured to modify the outgoing signal in response to a received input request or in dependence on a distance between a current position of a region of interest (ROI) of the patient (PAT) and a target area
(Continued)

(TA) in an imaging apparatus or in a radiation therapy apparatus.

12 Claims, 5 Drawing Sheets

(51) Int. Cl.
*A61B 6/03* (2006.01)
*A61B 6/04* (2006.01)
*A61B 6/46* (2024.01)

(56) References Cited

U.S. PATENT DOCUMENTS

| | | | |
|---|---|---|---|
| 9,901,263 B2 | 2/2018 | Hsiu | |
| 10,660,667 B2 | 5/2020 | Rohling | |
| 2009/0088659 A1* | 4/2009 | Graham | G06F 3/015 600/545 |
| 2010/0152545 A1* | 6/2010 | Ramsay | G06F 3/016 600/301 |
| 2012/0056733 A1* | 3/2012 | Ramsay | H04L 51/10 340/407.1 |
| 2014/0018664 A1* | 1/2014 | Weiss | A61B 5/72 600/414 |
| 2014/0152792 A1* | 6/2014 | Krueger | A61B 5/4863 348/78 |
| 2015/0196780 A1* | 7/2015 | Tijs | A61N 5/1049 600/1 |
| 2015/0352375 A1 | 12/2015 | Chen | |
| 2016/0019762 A1 | 1/2016 | Levesque | |
| 2016/0354112 A1 | 12/2016 | Kustra | |
| 2017/0018171 A1 | 1/2017 | Carter | |
| 2018/0102039 A1* | 4/2018 | Furuland | A61B 5/6892 |
| 2018/0151035 A1* | 5/2018 | Maalouf | G08B 6/00 |
| 2018/0268109 A1* | 9/2018 | Ramgir | G16H 40/67 |
| 2018/0296878 A1* | 10/2018 | Copelan | A63B 24/0006 |

FOREIGN PATENT DOCUMENTS

| | | | |
|---|---|---|---|
| JP | 2009076102 A | 4/2009 | |
| JP | 2011106860 A | 6/2011 | |
| WO | WO2010047435 A1 | 4/2010 | |
| WO | WO2013159787 A1 | 10/2013 | |
| WO | WO2014024115 A1 | 2/2014 | |
| WO | WO-2017038891 A1 * | 3/2017 | ............ B64C 13/18 |

OTHER PUBLICATIONS

Benjamin L. et al., "Rendering Volumetric Haptic Shapes in Mid-Air Using Ultrasound", Proceedings of ACM Transactions on Graphics, ACM, 2 Penn Plaza, Suite 701 New York, NY10121-0701USA, vol. 33, No. 6, Nov. 19, 2014 (Nov. 19, 2014), pp. 1-10, XP058060840.

Saga S. et al., "HeatHapt Thermal Radiation-Based Haptic Display", "Haptic Interaction", Lecture Notes in Electrical Engineering, vol. 277, pp. 105-107, Springer, Tokyo, (2015).

Carter T. et al., "Ultra Haptics: Multi-Point Mid-Air Haptic Feedback for Touch Surfaces", Proceedings of the 26th Symposium on User Interface Software and Technology, ACM Press, pp. 505-514, Oct. 2013.

Ochiai Y. et al., "Cross-Field Aerial Haptics: Rendering Haptic Feedback In Air with Light and Acoustic", CHI '16: Proceedings of the 2016 CHI Conference on Human Factors in Computing Systems, CHI '16: Proceedings of the 2016 CHI Conference on Human Factors in Computing Systems, p. 3238, May 2016.

Brandt E.H. et al., "Levitation in Physics", Science vol. 243, Issue 4889, pp. 349-355, Jan. 20, 1989.

Jun J-H. et al., "Laser-Induced Thermoelastic Effects Can Evoke Tactile Sensations", Scientific Reports 5, No. 11016, Jun. 2015.

Lee H. et al., "Midair Tactile Stimulation Using Laser-Induced Thermoelastic Effects: The First Study for Indirect Radiation", IEEE World Haptics Conference (WHC), Northwestern University, pp. 374-380., Jun. 2015.

Shinoda h. et al., "Airborne Ultrasound Tactile Display", The University of Tokyo, vol. 36, No. 3, pp. 207-210, 2018.

* cited by examiner

ULTRASONIC HAPTIC SYSTEM FOR PATIENT NUDGING

FIELD OF THE INVENTION

The invention relates to a system for patient positioning in imaging or radiation therapy, to a method for patient positioning in imaging or radiation therapy, to an imaging apparatus or a radiation therapy delivery apparatus including such a system, to an arrangement including such as system and an imaging apparatus or a radiation therapy delivery apparatus, to a computer program element, and to a computer readable medium.

BACKGROUND OF THE INVENTION

In medical imaging patient positioning is important. Without correct positioning, portions of a certain anatomy of interest (region of interest, ROI) may be cut off in the imagery thus rendering the imagery essentially useless. Re-imaging may be required which adds costs, increases waiting times and may also result in health hazards, for instance caused by additional x-ray exposure to patient or staff.

Currently, patients need to be positioned by medical staff in the imaging system as precisely and accurately as possible for best possible capture of the ROI. This may require experienced medial staff who have developed positional cues over time to help position the patient and help maintain correct posture throughout the imaging session. Sometimes (sub-)centimeter level final positioning of a patient is needed. For longer scan sequences, there may be a repeated requirement for such repositioning.

Achieving correct patient positioning may be cumbersome, especially in imaging systems where the patient resides in a tight enclosure such as in bores of CT (computed tomography) or MRI (magnetic resonance imaging) scanners. In particular, in case of MRI bores, the patient cannot easily be positioned inside the bore by medical staff due to the tight space constraints. Staff may not be able physically to reach inside the bore for giving physical instructions. Sometimes, because of the space constraint within the bore, all that staff can do is to give verbal instructions to the patient. But this may be inefficient because of language barriers or other communication challenges.

But even if there are no such space constraints, such as in certain chest X-ray imaging systems where the patient is standing in open space in between an X-ray source and a detector in an imaging room, positioning may still be cumbersome because staff will need to leave and reenter the room to assist in repositioning in-between different X-ray imaging sequences. This is because, especially with X-ray, staff cannot usually remain in the examination room during imaging due to hazardous X-ray dose exposure.

Similar patent positioning challenges may arise in radiation therapy (RT) delivery, where it must be equally ensured that the ROI is correctly positioned in the radiation beam to preserve as much healthy tissue as possible whilst destroying as much cancerous tissue as possible.

SUMMARY OF THE INVENTION

There may therefore be a need for a system or method to support patient positioning in imaging or RT.

The object of the present invention is solved by the subject matter of the independent claims where further embodiments are incorporated in the dependent claims. It should be noted that the following described aspect of the invention equally applies to the system for patient positioning in imaging or radiation therapy, to the method for patient positioning in imaging or radiation therapy, to the imaging apparatus or a radiation therapy delivery apparatus including such a system, to the arrangement including such as system and an imaging apparatus or a radiation therapy delivery apparatus, to the computer program element, and to the computer readable medium.

According to a first aspect of the invention there is provided a system for patient positioning in imaging or radiation therapy, comprising at least one transmitter configured to generate an outgoing signal capable of inducing, from a distance, a haptic sensation at an impact region on the patient's skin; and a control logic configured to modify the outgoing signal in response to a received input request or in dependence on a distance between i) a current position of a region of interest of the patient and ii) a target area in an imaging apparatus or in a radiation therapy apparatus.

In particular, the at least one transmitter is configured to generate from a distance an outgoing signal capable of impacting on a patient's skin, thereby causing the haptic sensation at the impact region on the patient's skin.

The outgoing signal generated by the transmitter propagates toward a portion of the patient's skin, the impact region. The system allows "ushering" or directing the patient to move an anatomy ("ROI"), such as an arm, knee or other, towards the target area, such as an imaging area, or so that the region of interest remains within the target area. Imaging or radiation therapy procedure can be conducted more efficiently. Interruptions due to repositioning can be shortened and can be carried our more precisely, in some embodiments without human user intervention. The target area may be 2D or 3D. The target area may be a portion of space in an imaging apparatus or radiation therapy apparatus. The target area may be a part of an examination region in the imaging apparatus or may be part of a treatment region in a radiation therapy delivery apparatus. According to one embodiment, the modifying by the control logic of the outgoing signal includes one any or more of: i) changing a position of the impact region relative to the region of interest (ROI), and ii) changing an intensity pattern of the outgoing signal. A pulsation of the signal may be changed for instance in dependence on the distance.

According to one embodiment, the control logic operates automatically or in response to the input request received through a user interface. According to one embodiment, the user interface allows remote controlling of the control unit.

According to one embodiment, the system comprises a localizer module configured to determine the current position of the region of interest. The localizer module and the control logic may operate together in a closed-loop system.

According to one embodiment, the localizer module is coupled to a receiver, the receiver configured to sense an incoming signal, wherein the localizer module determines the current position of the region of interest based on the incoming signal.

The transmitter TX and the receiver RX may be integrated into a single device, a transceiver.

According to one embodiment, the system comprises a conditioner configured to receive a measurement signal in relation to the patient, and wherein the conditioner is configured to modify the outgoing signal in dependence on the measurement signal.

In embodiments, the measurement signal is a vital sign, such as heart rate. In exemplary embodiments, the outgoing signal may be pulsed at a frequency below or above the heart rate to so induce a lowering of the respiratory rate. This allows calming down the patient, achieve better compliance and yet more efficient imaging. In embodiments, the vital sign is periodic and the outgoing signal may be pulsed out of phase with the vital sign. This further helps calming down patient. The measurement signal preferably describes a physiological or psychological state of the patient. The measurement is preferably acquired by a probe such as a pulse probe, ECG equipment, etc. Instead of using the outgoing signal, a different signal, issued from a different transmitter, may be used instead.

According to one embodiment, the control logic is configured to encode in the outgoing signal information to be communicated to the patient. The encoding may include generating a modulation pattern such as in a pulse by varying frequency and/or amplitude/intensity. Information such as instructions not necessarily related to the positioning may be so transmitted safely to the patient, even in the presence of noise or blocked vision. The code is pre-agreed with the patient. A semantic of the code may be displayed on a display device to assist the patient.

According to one embodiment, the transmitter is configured as at least one of: i) a midair ultrasound haptic transmitter, iii) an air nozzle, the outgoing signal being a jet of air, iv) an electromagnetic wave transmitter. The electromagnetic wave transmitter is in particular configured as a laser transmitter to transmit a laser beam. In general, as envisaged herein, the signal acts "over the-air", without physical contact (other than, in embodiments, through air) with the patient.

According to one embodiment, the patient resides in or at an imaging apparatus or resides in or at a radiation therapy delivery apparatus, such as a LINAC or other.

Specifically, patient may reside in a bore of the imager, such as in CT or MM.

The system does not need to be installed in the bore where space is already scarce thus improving patient comfort.

According to one embodiment, the imaging apparatus is any one of: an X-ray imaging apparatus, a magnetic resonance imaging apparatus, and a PET/SPECT imaging apparatus.

In one aspect, there is provided an imaging apparatus or a radiation therapy delivery apparatus including at least the transmitter as per in any one of the previous claims.

In another aspect, there is provided an arrangement comprising i) an imaging apparatus or radiation therapy delivery apparatus and ii) the system as per any one of the above embodiments.

In another aspect, there is provided a method of patient positioning for medical imaging or radiation therapy delivery, comprising:
  generating, with at least one transmitter, an outgoing signal capable of inducing, from a distance, a haptic sensation at an impact region on the patient's skin; and
  modifying the outgoing signal in response to a received input request or in dependence on a distance between i) a current position of a region of interest of the patient and ii) a target area in an imaging apparatus or in a radiation therapy apparatus.

In another aspect, there is provided a computer program element, which, when being executed by at least one processing unit, is adapted to cause the processing unit to perform the method.

In particular, the outgoing signal is generated from a distance (from the patient) and is capable of impacting on the patient's skin, thereby causing the haptic sensation at the impact region on the patient's skin.

In another aspect, there is provided a computer readable medium having stored thereon the program element.

The proposed system and method may be used for advanced positioning by giving patient feedback/advice, preferably in a closed feedback loop. The system may be used to reduce patient anxiety. In embodiments, the system may be used to influence breathing rate or heart rate by external, for instance ultrasonic pulses. The proposed system and method may be used to tune patient position and/or posture in an acquisition window of an imaging system to reduce scan time and/or enhance image quality.

The proposed system and method may be used with benefit in autonomous imaging systems or RT systems, during times when no medical staff is present.

Definitions

"user" a referred to herein is medical personnel at least partly involved in an administrative or organizational manner in the imaging procedure.

"patient" is a person, or in veterinary settings, an animal (in particular a mammal), who is be imaged.

"ROI" (region of interest) relates to a part of the human body, internal or external, but may also relate to the whole of the patient's body, in which case some or each part of the body is a region of interest. In general, the ROI is the subject of interest of the (image-based) medical examination.

BRIEF DESCRIPTION OF THE DRAWINGS

Exemplary embodiments of the invention will now be described with reference to the following drawings which are not to scale, wherein.

DETAILED DESCRIPTION OF EMBODIMENTS

Figure 1:
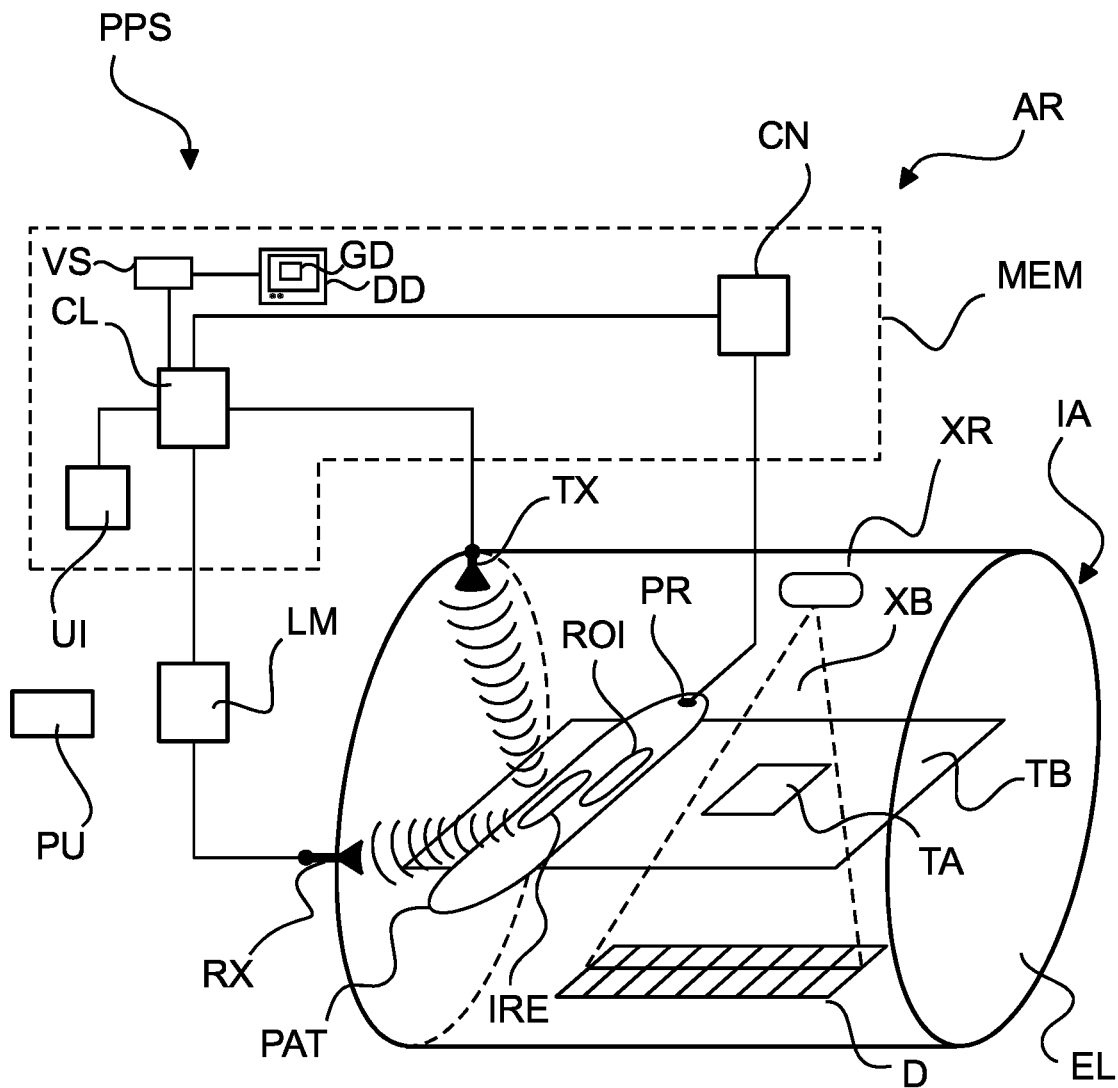
FIG. 1 shows a block diagram of an arrangement including a patient positioning system.

With reference to the schematic block diagram in FIG. 1, there is shown an arrangement AR as envisaged herein including a computerized system for patient positioning PPS and, in some embodiment, an imaging apparatus IA. The imaging apparatus IA envisaged herein in embodiments includes emission based imaging or transmission based imaging but also includes ultrasound imaging or magnetic resonance imaging MM.

In embodiments, the imaging apparatus IA is configured to acquire medical imagery of internal structures of the patient PAT. The medical imagery may reveal inner organs of the patient. Alternatively, instead of anatomic-structural imaging such as in X-ray or MM, functional imaging is also envisaged. Functional imaging allows visualizing, for instance, metabolic activity as in some types of nuclear emission imaging, such as SPECT or PET. In either case, the medical imagery may assist in therapy or diagnosis of the patient PAT.

In broad terms, and turning first to the imaging apparatus IA in more detail, this includes, in embodiments, equipment to generate an interrogating imaging signal. The interrogating imaging signal interacts with tissue inside the patient. Patient tissue modifies the interrogating signal and causes a modified signal. The so modified signal encodes information about the internal structures, anatomies, functional activity, etc, of the patient. The modified signal can be detected by a detector unit D.

One embodiment for transmission imaging in particular envisaged herein is X-ray based imaging such as radiography, C- or U-arm imaging or computed tomography CT imaging ("CT scanner"). In these embodiments, the interrogating imaging signal is an x-ray beam XB. In this embodiment, the equipment to generate the X-ray beam includes an X-ray source XR, such as an X-ray tube. The X-ray source is energizable to release the x-ray beam in an otherwise known manner. The x-ray beam passes through the patient, is then modified, in particular attenuated, and the so modified beam is then detected at an x-ray sensitive detector D.

The x-ray sensitive detector D is arranged opposite the x-ray source to form an imaging region in between the two where the patient resides during the imaging. The term "imaging" as used herein is the period throughput which the interrogating imaging signal, such as the x-ray beam, passes through the patient and is detected at the detector D. Intensity data registered at the detector D can then be processed by suitable circuitry into internal anatomical or functional images. For instance, in CT cross sectional x-ray images can be obtained from the detected X-ray intensities. The imagery may be rendered for visualization on a display device to assist clinical personnel. In the emission embodiment, the equipment to generate the interrogating imaging signal resides within the patient, after suitable administration prior to imaging. The equipment may include a suitable radioactive tracer substance. The tracer substance interacts with patient tissue from within, then egresses the patient and is then detected by detectors arranged outside the patient, at last partially surrounding the patient, as is in PET or SPECT and similar imaging techniques.

In MRI, the detecting unit D comprises one or more radio frequency coils that are capable of picking up radio wave signals. The radio wave signals are emitted by disturbed protons in patient tissue when relaxing back into alignment with a strong magnetic field generated by the MM imager during the imaging.

Some of the described imaging apparatus IA embodiments, but not necessarily all, may include a physical enclosure EL that surrounds the patient during imaging. The patient resides within the enclosure EL during imaging, possibly lying or sitting on a support such as an examination table TB inside the enclosure. CT scanners and MM scanners may include such enclosures arranged as a bore. The bore is relatively tight and does not leave much space for the patient to move. Whether or not the imaging apparatus includes an enclosure, in all embodiments the imaging apparatus IA is in general situated in a specific imaging room. Medical personnel are usually not in the imaging room whilst the imaging is ongoing. This is because staff need to be protected from un-necessary x-ray exposure for instance or because the imaging apparats operates in autonomous mode as envisaged herein in embodiments.

So that the imaging procedure is made more efficient and to maximize information captured in the imagery, it may be important that the specific organ of interest, also referred to herein as the region of interest ("ROI"), is positioned in a designated target area TA during the imaging. The target area is a portion of either 2D or 3D space. Specifically, the target area is a portion of 2D or 3D space in the examination region. In imager IA embodiments that include a patient enclosure EL, the target area TA is at last partly or wholly inside the enclosure.

In order to better support patient positioning, to accomplish this quicker, easier and more efficiently, the imaging arrangement AR includes a patient positioning system PPS, referred to herein as the "PPS". In broad terms, the PPS includes one or more transmitters TX mounted at or inside the imaging enclosure EL, eg the bore, or at least mounted within the imaging room. The PPS allows manual or fully automatic operation of the transmitters TX. In operation, the transmitter TX is energized to emit a signal towards the patient whilst the patient is in the examination region or, in embodiments, is inside the enclosure EL. The signal emitted by the transmitter TX causes, from a distance, without physical contact with the patient, a haptic sensation on the patient's skin at a certain impact region IRE.

Embodiments for causing such haptic sensations include in particular ultrasound transmitters TX. In such embodiments, the one or more transmitters TX are configured to cause a directed or focused ultrasound beam which can be directed to desired impact region IRE on the patient's body PAT. The direction of the ultrasound beam is automatically or manually adjustable to impact a desired impact region IRE as will be explained more fully below.

The frequency and/or intensity of the ultrasound waves emitted by the transmitter are such that they are capable of simulating mechanoreceptors situated in the patient's skin. It is not necessary for the patient to expose bare skin for this, because the ultrasound waves are capable of coupling-in onto the skin through a suitably thin garment such as hospital gowns usually worn by patients.

The action of the signal emitted by the transmitter TX is such that it encourages the patient to move to the desired position so that the region of interest is, or remains, within the target area TA. Essentially, the transmitter TX can be used to nudge or usher the patient, through the emitted signal, so that patient assumes the correct position and that the region of interest is within the target area TA or, as the case may be, that the ROI remains within the TA. In the following, the described signal emittable by the one or more transmitters TX may be referred to herein as the "nudging signal". Using an ultrasound transmitter as described is one preferred embodiment, but other types of transmitters using other physical principles are also envisaged herein, in addition or in the alternative. The PPS may include a control logic CL that controls any one of an intensity, frequency and direction of the nudging signal.

As mentioned, a plurality of such transmitters TX may be spatially suitably arranged in/or at the imager, in particular inside its enclosure (if any) and/or may be suitably distributed in the examination room. Preferably, the arrangement of the one or more transmitters TX is such that, once the patient is inside the examination region, one or more portions of the patient's skin can form an impact region IRE for the nudging signal. This may be achieved for instance by having the one or more transmitters arranged spatially suitable in relation to the examination region. The transmitters may be arranged inside the examination region, inside the bore, and/or around the examination region. In addition, one or more of the transmitter may be moveable in different spatial orientations. The transmitters may be mounted using a joint, articulated arm, a track or other arrangements that allow movement, including translation and/or rotary movement. In embodiments, a single transmitter may be sufficient if arranged at a suitable vantage location and/or if allowed sufficient motional degrees of freedom. The movement of the transmitter is effected by the control logic. Specifically, the control logic instructs suitable actuators to adjust an orientation of the transmitter, and hence the direction of the nudging signal emittable by the transmitters. Suitable actuators may include any one or more of servo or stepper motors including mechanical gearing, hydraulics, piezoelectric-element(s), any combination of the foregoing, and/or others.

Turning now first to the manual embodiment of the PPS as envisaged herein and as mentioned before, the control logic CL may be responsive to commands received from a user interface UI. Preferably the user interface UI is arranged as a joy stick arrangement although other embodiments are also envisaged such as a touch screen, keystroke based interface and any other.

The user interface ("UI") is preferably arranged remotely away from the imaging apparatus, for instance outside the imaging room. Alternatively, the UI may be arranged inside the room, in embodiments shielded in a cubicle where the user can safely operate the user interface without exposure to potentially hazardous imaging signals. If multiple transmitters TX are arranged, the user interface UI may include user interface elements that allow the user to select and switch between the different transmitters TX to select a spatially suitable one from which to issue the nudging signal. In this manual embodiment the user may be positioned so that relative anatomies in relation to the ROI are in line of sight in order to efficiently steer the transmitter to achieve a desired direction from which the nudging signal issues. If direct eyesight is not possible, due to structural occlusions (eg, the bore) and/or posture of the patient, the user may be supported by a surveillance or monitoring system such as a video camera system that includes sensors RX. The one or more video cameras RX may be arranged in the examination room, suitably arranged around the examination region of the medical imager IA. in particular, the one or more video cameras may be arranged at the imaging apparatus. One or more of the cameras may be arranged inside the enclosure or similar so that the patient position and posture, and hence the current location of the ROI can be ascertained by the user. Based on the video camera footage, the user can then request through the UI a suitable re-positioning of the transmitter TX. Issuance of the nudging signals may then be requested through the UI to direct the nudging signal to a suitable region of impact and so urge the patient to move or repostue such that the ROI is moved towards, or remains inside, the target area TA.

The described embodiment of inducing haptics at a distance by way of ultrasound, such as mid-air haptic systems, have been described elsewhere for the purpose of computer games. See for instance, B Long et al, "*Rendering volumetric haptic shapes in mid-air using ultrasound*", published in Proceedings of ACM SIGGRAPH Asia 2014, "*ACM Transactions on Graphics*", vol 33(6), 2014).

Ultrasound based haptic system have been found by Applicant to be of particular advantage as patients react positively to perceived touch, touch being a fundamental sensory input for spatial clue and positioning. Efficient guidance of the patient to fine tune his/her posture is thereby effected. The sensation of touch caused by the ultrasound waves emitted may also act in a calming manner on the patient. If the ultrasound waves are applied at a suitably chosen impact region IRE (on which more further below), user can any one of easily, intuitively, unambiguously, quickly direct the patient to assume the correct position.

Turning now in more detail to the ultrasound embodiment, the transmitter TX may be arranged as a one or two dimensional phased array of ultrasound transducers. The ultrasound transducers are controlled by the control logic CL in a manner so as to create an acoustic interference pattern that gives rise to the directed ultrasound beam that is capable of inducing the haptic sensation on the patient's skin at the impact region IRE. The focused ultrasound waves cause, at a distance and in a non-invasive manner, sound sensations at any desired intensity and/or frequency. In embodiments, the acoustic field created by the phased array allows forming volumetric acoustic fields, "haptic shapes", such as a palpable sphere or other geometrical configurations. When applied to the patient at the impact region IRE the patient then experiences a sensation as if a physical object of the specified shape is in skin contact. Suitable acoustic shapes such as the mentioned spheres may be used to create a pleasant massage effect for instance, to gently nudge the patient towards the desired target area.

Useful as the described ultrasound embodiments of the transmitter TXR are, these are not at the exclusion of other embodiments that are not necessarily ultrasound based. For instance, in other embodiments one or more air nozzles can be used instead as transmitter TX. In this embodiment the transmitter TX issues a jet of directed air to thereby cause the haptic sensation and to effect the nudging. In yet other embodiments, one or more electro-magnetic radiation based transmitters TX are used that are configured to cause haptic sensations. Specifically, the electro-magnetic radiation is configured to excite mechanoreceptors embedded in the patient's skin. In exemplary embodiment of the concept, the nudging transmitter TX may be arranged as a laser transmitter operable at a suitable frequency. An electromagnetic field such as laser light can also create a haptic effect at a distance from the source of excitation. In embodiments, pulsed laser based systems are used. In embodiments, nanosecond laser is used, which, when applied to the skin, evokes tactile sensation. In embodiments, heat radiation may be used. Certain receptors (eg, TRPV1) in human skin respond not only to heat but also to pain. By eliciting both responses in turn, a haptic sensation can be caused. This may be achieved by controlling a heat source, such as a halogen lamp or other. The heat source is suitably focused using one or more reflectors and the focus is rapidly switched. See for instance Saga S. "*HeatHapt Thermal Radiation—Based Haptic Display*", in: Kajimoto H., Ando H., Kyung KU. (eds), "*Haptic Interaction*", Lecture Notes in Electrical Engineering, vol 277, pp 105-107, Springer, Tokyo, (2015). The above mentioned transmitter TX embodiments can be used singly or in combination or in any sub-combination.

In embodiments, the nudging signal may be pulsed. In any of the above mentioned embodiments, the frequency of the single, the frequency of the pulses and/or intensity of the nudging signal may be held constant throughout the nudging operation but may also vary in other embodiments. In more detail, the intensity of the nudging signal may drop, the closer the region of interest is to the target area TA. Proximity information may in addition or instead be modulated by varying a frequency of the pulsation of the nudging signal. The pulse frequency may drop the closer the distance between ROI and target area. In a similar, manner the frequency of the US signal itself may be changed.

In embodiments, once the region of interest is in the target area, that is, once the patient has assumed the correct position, no more nudging signals are issued by the transmitter TX. In embodiments, once the patient moves, that is once there is motion of the ROI within the target area, the transmitter TX is re-activated to encourage the patient to assume a posture so that the region of interest remains within the target area TA. If a portion of the region of interest extends outside the target area, the direction and/or intensity and/or pulse frequency of the nudging signal may be changed accordingly, in dependence on the distance between a current position of the region of interest and the (in general fixed and known) position of the target area TA.

In the above described embodiments, any one or a combination of the direction, pulse frequency and/or intensity of the nudging signal may be effected by the control logic in response to commands received through the user interface UI. However, in other embodiments, the control logic CL controls the transmitter TX automatically, in particular autonomously, based on a location signal in relation to the patient and/or the ROI. In particular, the control logic is configured to change any one or all of the direction and modulation of the nudging signal based on a distance between the current position of the ROI and the target region TA. Changing the modulation in this manner includes any one or all of changing the pulse frequency of the nudging signal, changing the intensity of the nudging signal, and changing the frequency of the signal. Such fully automatic embodiments, or at least semi-automatic embodiments, as envisaged herein for autonomous imaging ask for no or low level of user action during or in between imaging. In particular, in autonomous embodiments, the PPS includes a locator module LM that is configured to establish, based on the location signal, the current position of the patient, in particular the current position of the region of interest. The location signal may be received through a receiver RX.

The current position of the ROI may be defined relative to a world co-ordinate system. The world coordinate system may also be used to establish the position of the detector and/or the imaging signal source, such as the x-ray source.

The target area may be defined as a patient envelope. This is a portion of space, suitably de-marked by virtual or real demarcations. The locator module LM is suitably configured to be aware of the spatial extent of the patient envelope. A number of different embodiments are envisaged for the localization module LM. In embodiments, if one part of the ROI extends outside the envelope TA, this is targeted by the transmitter at a suitably chosen impact region IRE to urge the patient to move the extending body part so as to retract within the patient envelope.

In more detail, the target area TA may be defined by a patient position marking system. The marking may provide in embodiments two functions: (1) it defines the boundary within which patient or at least the ROI should remain, and (2) it defines scan specific patient position. The marking can be in terms of physically defined boundaries or virtual markings, or may be implemented via optical projection system or in a remote system visualized as 3D contour. The patient position boundary, defined by the patient position marking system, includes the above mentioned patient envelope. The envelope may be defined in 2D or in a 3D spatial matrix coordinate system based on patient and scan type and specific scan sequence within the scan type. The spatial matrix represents the contour of the envelope.

As briefly mentioned above, in embodiments the PPS includes the receiver RX suitably positioned to receive an incoming location signal from the patient and this incoming signal is then processed by the localization module LM to establish the current position of the patient, in particular of the region of interest. The incoming signal may be an at least partial back-reflection signal or a back-scatter signal of, in particular, the outgoing nudging signal. The nudging signal may hence be used in embodiments in a dual role: for nudging and ROI location.

In embodiments, the RX includes an optical camera or video based system, similar to what has been described above in relation to the manual embodiment where the user is provided with live footage. In distinction from the manual embodiment, in the automatic/autonomous embodiment, the incoming location signal as received by the receiver RX is automatically processed by the locator module LM into current ROI position information.

In embodiments, light sensitive sensor RX of the camera is configured to receive back scattered light caused by surrounding light scattered off the patient. A camera system with a depth sensing or heat sensing (IF) sensor be used in addition or instead of the described optical sensor cameras.

The imagery obtained by the location resolving sensor RX is suitably registered by the locator module LM to the world coordinate system. An image recognition component in the locator module may be used to analyze the captured imagery to identify in the imagery the patient and, in particular, the region of interest. The region of interest may be defined geometrically by a geometric shape that surrounds the region of interest suitably tight. Once the ROI or another anatomy having a known distance to the ROI, has been identified by the locator module LM in the imagery of the receivers RX, the in-image location is mapped to the world-coordinate system. Because the location of the target TA is a prior known in world-coordinates to the locator module LM, the relative distance between the ROI and the TA can be computed by taking the Euclidean distance. When setting up the PPS, the location of the one or more cameras RX and their magnification may be used in a prior calibration with the world-coordinate system, so that the locator module can map the image information to real world distance for the ROI-TA distance. Similar 3D or 2D geometrical computations may also be applied when using localization modules LM which operate based on different localization principles.

In particular, in the ultrasonic embodiment described above it is the ultrasound signal itself that is used for both nudging and location purposes. Echo location may be used in embodiment to establish the ROI-TA distance. The control logic may control the transmitter TX to operate in either of two modes, a nudging mode or in location mode and to switch rapidly between the two as required. When operating in location mode, the frequency of the TX-emitted ultrasound may be changed so that no nudging sensation is induced in the patient's skin. The outgoing ultrasound wave directed from the transceiver is emitted and reflected back and received as an incoming signal at the receiver RX. An evaluation of an incurred Doppler shift may then be used to establish the position of the region of interest. In this and other embodiments, the receiver RX and the transmitter TX may be arranged combined into single unit, a transceiver. As before, and as explained in terms of the optical camera or video based embodiments for the receiver RX, the so found ROI location can be mapped into the world co-ordinate system to establish the relative distance between the target area and the current position of the region of interest. In other words, in this and in similar embodiments, the ultrasound system may be used as a closed-looped control system. Specifically, the location of the region of interest is monitored and in response to the current position of the ROI, and hence of the relative distance to the target region, the nudging signal is adapted by changing modulation and/or direction. In particular, a direction of the nudging signal and/or (pulse) frequency and/or intensity may be suitably modulated in dependence of the measured ROI-IRE distance.

As mentioned above, once the region of interest is within the target area the nudging signal subsides, but the locator module LM may continue to monitor the ROI position. If the location module registers motion of the region of interest within the target area, the nudging mode is switched into, and the nudging signal is re-issued to encourage the patient to move or reposture so that the region of interest remains within the target area TA.

In closed-loop embodiments, whilst the ROI remains within the target area TA, the nudging mode remains off, but switched back into once at last a part of the region of interest extends beyond the target region, for instance extends beyond the patient envelope. Although the closed-loop system has been described with particular reference to the haptics-through-ultrasound transmitter TX, non-ultrasound system such as the air jet or laser embodiment may also be arranged in closed-loop fashion along the lines described above.

Figure 2:
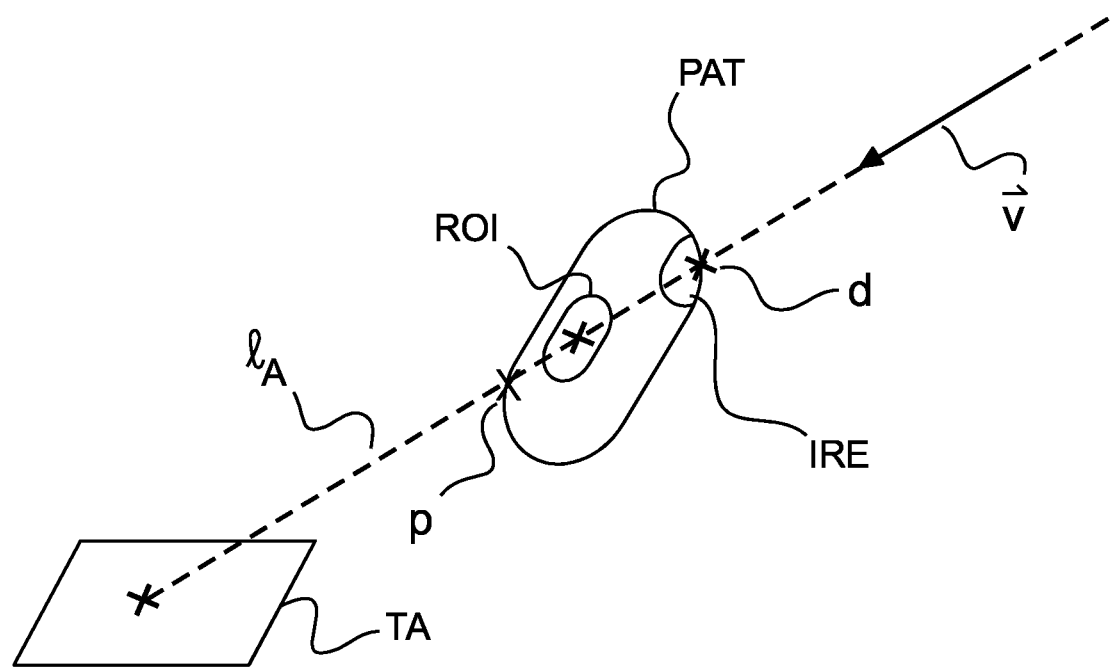
FIG. 2 shows a schematic illustration of a mode of operation of the patient positioning system.

Reference is now made to FIG. 2 which illustrates operation of the control logic CL. More particularly, FIG. 2 illustrates how the impact region IRE is defined where the haptic sensation is to delivered so as to nudge the patient to assume the correct position. As used herein, the patient position or posture is correct, if the region of interest is at last partly, preferably fully, in the target area TA. The impact region if so chosen, so that the patient is guided, ushered or nudged to perform a motion, or a change of posture, so that the ROI moves towards the target area or such that the ROI remains within the target area TA. Broadly, the control logic CL is configured to generate the nudging signal so that this acts from the "back" onto the patient so as to encourage the patient to assume the correct position. In more detail, given a current position of the ROI (determined as explained above) and the, in general fixed and known, position of the target area TA, an imaginary line (shown dashed) of action $l_A$ may be defined to pass through the target area and through the ROI at the current position thereof. The line of action $l_A$ extends through the patient PAT. Because the patient has a three dimensional shape, this line of action will intersect the surface of the patient at two points, a proximal one ("p") and a distal one ("d"). The proximal position p is closer to the target area TA than the distal position d. It is preferable then that the impact region IRE is located at said distal portion d. Control logic CL is hence configured to operate the transmitter TX so that the directed outgoing nudge signal propagates along the line of action in a direction v̄ towards the target area with the region of interest situated in between the impact region IREC and the location of the target area.

The geometric principle in FIG. 2 may be illustrated by the following example where, say, a knee joint is to be imaged at a specific position—for example when flexed at a given angle and positioned at the target area TA at the center of the scanner bore in order to get the best image quality. In this case the operator can first check if the knee position is aligned correctly to the patient position marking system. If this is not the case, one or more haptic pulses could be applied to at a distal point (d) on the side of the knee opposite to the desired movement direction. Such a nudge should persuade the patient to move the knee away from the nudge position—i.e. in the desired direction. Similarly, if the knee position is correct but the flex angle wrong, nudges directed at the calf or foot will assist the patient in correctly adjusting the flex angle. As may be readily appreciated, if a series of scans are required (for example at different flex angles) the nudging could be repeated at several times during the scan sequence (for example between scans)— without having move the patient from the bore.

A spatial coordinate of the impact region, such as its center or any other reference point, may be established by three dimensional geometry computations, once the current location of the ROI and the location of the target area is known in the world coordinate system, using the geometric principle explained above in FIG. 2.

It may also be preferably to know three dimensional shape of the patient, at least in approximation. For instance, for the above operational purpose of the control logic CL the patient's body may suitably be approximated as a cylinder for instance. Once the position of the impact region is established, such as the above described distal point d, an area such as a disk or of any other geometric shape may be defined. This area is the impact region IRE. A suitable one of the transmitters (should there be more than one) is then activated and oriented so that the outgoing nudge signal propagates along the current line of action and impacts onto the patient's skin at the so defined impact region IRE. It will be understood that in practice, the location of the IRE may change with patient motion to effect real-time nudging. The above described geometrical computation of the impact region IRE location based on the line of action principle as per FIG. 2 is an exemplary embodiment, and other embodiments may also be used instead, harnessing other sources of information.

Figure 3:
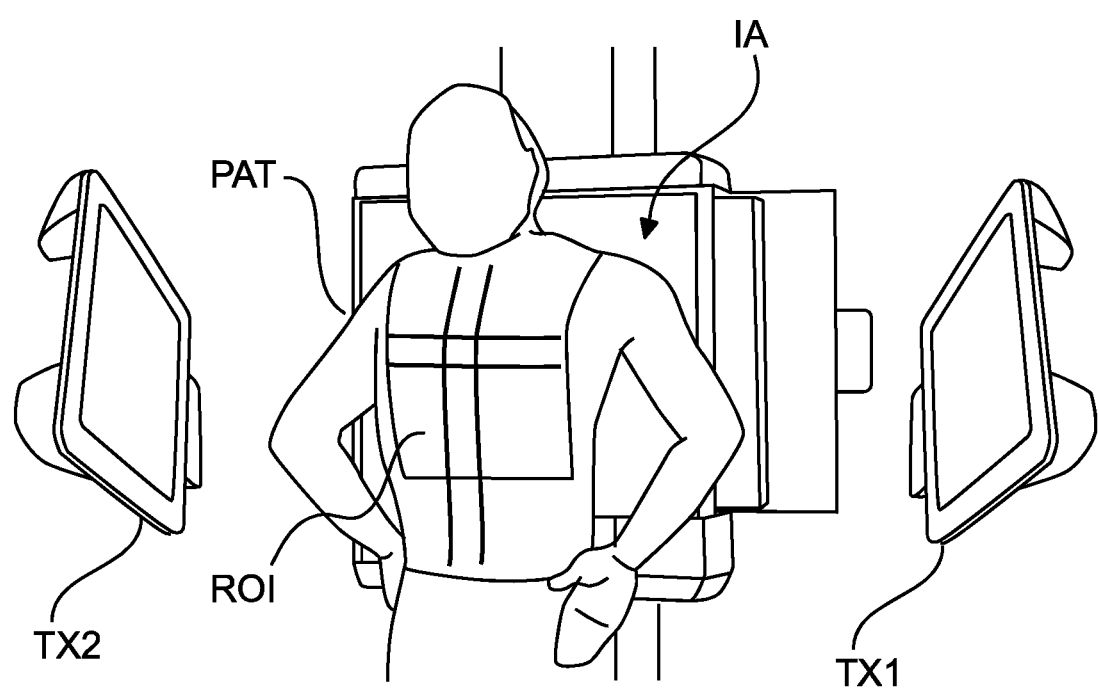
FIG. 3 shows an imaging apparatus including a part of the patient positioning system according to one embodiment.

Reference is now made to FIG. 3 which shows aspects of the proposed imaging arrangement, including an imaging apparatus IA, as represented here, without a patient enclosure EL. The imaging system shown in FIG. 3 is suitable for instance for chest imagery where the x-ray source (not shown) is arranged opposite the detector D. The detector D may be wall-mounted or mounted on a stand inside the examination room. The height of the detector D can be changed to accommodate different patient sizes. In this embodiment the patient may stand during the imaging inside the examining region, rather than lying on a support as indicated in the exemplary embodiment of FIG. 1. Two (or more) nudge signal emitting transmitters TX1 and TX2 may be arranged on either side of the patient. The emitters may be likewise wall mounted in the room or may be mounted or arms of other structures attached to the imaging apparatus.

The transmitters shown in FIG. 3. are of the ultrasound type with the phased array of ultrasound transducers arranged on respective panels. Two such panels are shown, by there may be more or less. Each panel may be moveable by suitable actuators so that the panel can be reoriented. The transmitter(s) TX1,TX2 is then energized and the train of focused sonic waves propagate along the line of action towards the impact region. As shown in the Fig., a portion of an envelope, in this example the patient's skin surrounding the lungs ROI, may be visualized using light projected onto the patient's back. In the illustrated example, a cross may be projected onto the patient's back.

In one embodiment, there are preferably four transmitters, one TX1,TX2 at either side of the patient, and two more, one in front (on the detector side) and one behind the patient at the X-ray source side XR. For instance, if the patient moves to far off to the left (towards transmitter TX2), transmitter TX2 is activated, as per the principle of FIG. 2, to so urge the patient to the right towards where the other transmitter TX1 is positioned, to encourage a motion so that the lungs ROI are repositioned in the target area. The target area TA in FIG. 3 may be thought of as a patient envelope in form of a section of a cylinder extending from the floor upwards towards the ceiling. A diameter of the cylinder may be chosen as the girth of an average patient. The intersection of this cylinder with the floor may be visualized as a painted contour on the floor, such as a circle, or a circumscribing square etc. It may be possible to use less than four transmitters, like three, two or a single one, but then to have a motorized arrangement in place so the transmitter can orbit around the patient so that the impact region IRE can be well defined for most, if not all, positioning requirements.

Figure 4:
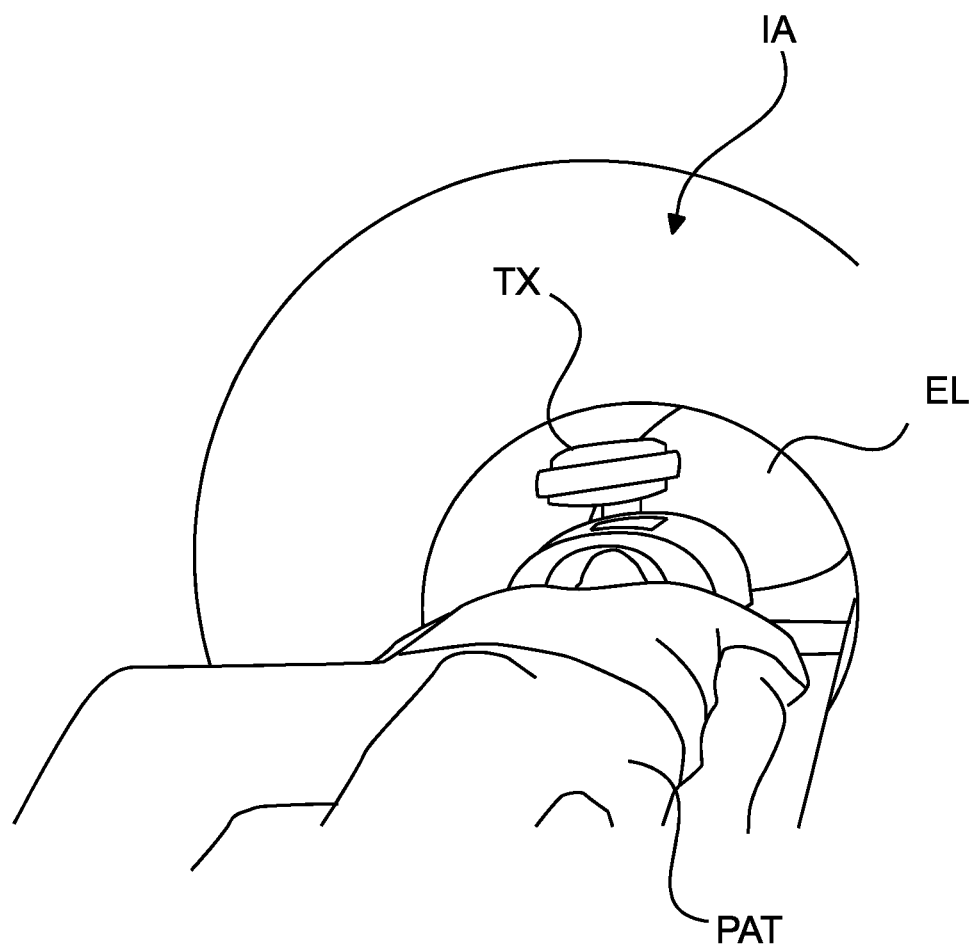
FIG. 4 shows an imaging apparatus including part of the patient positioning system according to a second embodiment.

FIG. 4 shows an embodiment of the imaging apparatus where the transmitter TX is arranged inside an enclosure such as a CT bore or (as shown) MM bore. In this these or similar embodiments such as PET, the patient is lying on the examination table TB inside the bore EL. In embodiments, the transmitter may be positioned on top of the region of interest, in this case over the patient's head. If the patient moves their head outside the target area, the nudging signal is applied, preferably heeding the principle of FIG. 2. The transmitter may be slidable along a longitudinal axis of the bore, for instance on a track to be used for different ROIs or imaging protocol. Circumferential motion along the bore's curvature may also be envisaged so that the transmitter may be positioned not only on top of the ROI but to either side, left or right. In addition, the transmitter may be re-orientable to increase directional scope. In embodiments, the transmitter is mounted in a head coil as may be used in head MM imaging and as exemplary shown in FIG. 4.

Although the above described patient positioning system PPS may be used in a completely automated autonomous fashion, it may still be combined with some user interaction facility. For instance, it may be desirable to have a user from a remote location be in contact with the patient during the imaging through video link and/or audio connection with a microphone and a speaker suitably arranged.

In embodiments there may also be a conditioning element CN that allows to modulate the nudging signal to perform breathing control. For instance, the transmitter TX in the haptic ultrasound or air nozzle embodiment, may be controlled by control logic CL to issue a pulsed ultrasound-signal with frequency and/or phase adjusted in dependence on vital sign measurements. Suitably pulsing the ultrasound signal may lower respiratory rate (RR) thus acting in a calming manner on the patient. In particular, in embodiments a probe PR such as a blood pressure measuring apparatus or a pulsometer may be used to acquire the vital sign data of the patient whilst he or she is at or in the imaging apparatus. The vital sign measurements may be obtained during imaging or in between the imaging.

Vital sign readings can be used to control the frequency of the pulsed signal emitted by transmitter TR. The control module may hence switch into a RR-control mode to control RR rate. The RR-control mode may be applied during the patient positioning by modulating the nudging signal during the patient positioning. Alternatively, or in addition, the RR-mode may be applied once the patient's ROI is within the target area TA. For instance, once the patient has been suitably positioned, the control unit CL may instruct the transmitter TX to operate in the RR-control mode where the haptic sensation signal is now induced on the patient's skin not for the purposes of positioning through nudging that, but to calm the patient by encouraging to lower the RR.

The pulsed signal emitted by the transmitter TX may be modulated in dependence on the acquired vital sign readings. In particular, the frequency of the RR-control signal emitted by the transmitter TX may be adjusted by the control logic CL to be lower or higher than the frequency of the current heart rate or in dependence on blood pressure readings. Both, heart rate and the blood pressure readings are known to be correlated with the current RR of the patient. Adjusting the RR-control pulsed signal to that the RR-control pulse is in particular lower than the current heart rate of the patient may induce a lowering of the RR, thus calming down the patient. Lowering the RR, may in turn lower heart rate or blood pressure, thus adding to the calming effect. In addition, it has been found that to have the pulsation of the emitted RR-control signal out of phase of with the heart rate may also induce a lowering of the RR. In other words, the haptic system can also be used for controlling not only the position as described above, but also control the RR of the patient. Operation of in this RR-control mode may be done once the patient is suitably positioned or may be done during the nudging operation. The initial RR provides the starting point and the desired RR provides the final end point. The acoustic haptic system can be used to provide haptic feedback, which mimics the RR breathing pattern, which is slightly out of phase of the RR breathing pattern. This will shift the current RR into the haptic system phase. The haptic system is again triggered to bring the haptic feedback pattern slightly out of sync with the current RR pattern, since respiration rate cannot be induced to a desired level immediately, this has to be achieved in steps. This will provide a continuous ascent and/or descent of RR to the desired level before imaging.

In addition or instead of modulating the transmitter TX signal for RR-control as described above, the control logic may be switched into a touch mimicking mode, to mimic human tapping or patting. The control logic CL may be used to modulate a touch pattern, mimicking periodic and rhythmic touch to calm down the patient especially children. A rhythmic touch can act as an assurance of presence for reducing anxiety during imaging. Switching into touch mimicking mode, can be done during nudging or, preferably, once the patient is correctly positioned. The control logic may switch into the touch mimicking mode automatically based on vital sign readings that suggest a state of anxiety of the patient, such as increase in blood pressure or heart rate for instance. The touch mimicking mode may also be used in the manual embodiment. If the user believes the patient is upset, the user interface may be operated to switch into the touch mimicking mode and to apply the signal accordingly to calm patient down. The haptic ultrasound or air jet transmitter TX, may be controlled by control logic CL to issue a pulsed US-signal so as to mimic human patting or tapping.

It will be understood that if the controller CL is operated in touch mimic or RR-control mode, the impact region IRE may not necessarily be defined as described in FIG. 2. The impact region could be anywhere but applying the signal to the patients back or shoulder may be advantageous.

It will further be understood that in embodiments all the above mentioned functionalities, that is, the nudge signal generation, the position of ROI determination, the RR-control signal generation, and the touch mimicking mode may all be administered through the same set of one or more transmitters TX as controlled by a single control logic CL. The control logic may be configured to switch through modes of operation to administer each of these functionalities. This allows a compact build. However, alternative arrangements are also envisaged where some or all of the above mentioned functionalities are administered through respective one or more different transmitters and/or where respective control tasks are distributed across a set of two or more different control logics. In one extreme embodiment, there may be up hence up to four different control logics, each dedicated to a single one of the functionalities, and possibly each using a different transmitter. In the alternative, transmitter sharing may also be envisaged in such embodiments.

Some or all components of the PPS may be embodied as hardware or software either on a single processing unit PU or distributed across a plurality of processing units. Some or all of the components of the PPS may reside as software modules in memory MEM or may be distributed across a plurality of such memory units. In particular, the control unit may be arranged as an ASIC or FGPA integrated into the imaging apparatus. The transmitters and/or the receivers, if required, may be arranged in or at the imaging apparatus, in particular inside the bore, or may be arranged suitably around the imaging apparatus in the imaging room such as wall mounted, ceiling mounted or floor mounted as required. Although the components of the PPS are shown in the enclosed Figures as separate functional units, some or all of them may be in fact integrated into a single processing unit.

In embodiments, the control logic is configured to modulate onto the nudging signal further information intended for the patient. The information may be modulated by frequency and/or amplitude modulation or other to cause a modulation pattern that represents the "code". The nudging signal thus encodes the information in the modulation pattern. In this manner, a coded haptic signal may be created by the control logic CL. A display device DD may be mounted inside the bore, or outside of the bore, but in either case so as to have its screen visibly exposed to the patient at least at times whilst the patent is in the imager's bore. A graphics display GD may be generated by a visualizer component VC and displayed on the display device DD. The graphics display GD represents a "semantic" of a specific modulation pattern in terms of explanatory text and/or imagery. The displayed text or imagery explains, "decodes", for the patient what the modulation pattern, the encoding, means.

The coded haptic signal may be used with benefit during imaging procedures, not only for imparting instructions such as "Breath hold", "Stay still", but also in relation to providing other information on imaging or imaging supporting clinical procedure to be performed. For example, the patient may be pre-informed by the coded haptic signal that a contrast is going to be injected, that the patient can expect a hot sensation/cold sensation, etc. Patients may not be able to hear verbal instructions due to noisy environments or may not be always able to read information off the display when their head is within the bore or if they have to assume a certain posture for taking an x-ray etc. However, with the coded haptic signal, the information can be communicated easily in these circumstances.

The coding may be done by administering the haptic signal in pulses. Possible modulation patterns may include any one or more of the following: different count of pulses, either absolute or per unit time (frequency), different intensities (amplitude), different durations of the application of a sequence of pulses. The encoding may also include exposing a certain body part, but now not for the purpose of positioning, but to communicate information. Thus the targeting with the haptic signal different body parts represents different information/instructions.

Any one of the above mentioned patterns may encode any one of the following: a positioning request, an amount by which a certain body part should be moved/shifted/turned etc, an indication that a procedure is underway etc.

The different targeting of body parts may be used to indicate moving or repositioning etc, or to indicate any other agreed information.

In addition, the haptic code pulse may be used for pain evaluation or localization, for example by increasing thrust. This may be useful for quantitative evaluation pain or similar.

In addition or instead to the above mentioned options, the haptic signal may be used for compliance/cooperation checking. After delivering the instruction/information to the patient by application of the coded signal (eg, pulse), there is a period of post-instruction timeout. Specifically, once the coded haptic signal has been sent to the patient, the control logic will switch into a wait mode for a pre-set timeout period. This timeout period is the expected time it would take the patient to react to the signal. If there is no response, the signal is again applied, with a further timeout and so on. In case the patient repeatedly fails to abide by the instructions then the system may ask for human intervention. The proper response may be checked for example by still or video-camera surveillance with machine learning based processing to check for correct response by patient.

The code could be fixed all the same for all patients. Alternatively, the code is patient specific or application specific to meet patient's requirements for best user interfacing.

Figure 5:
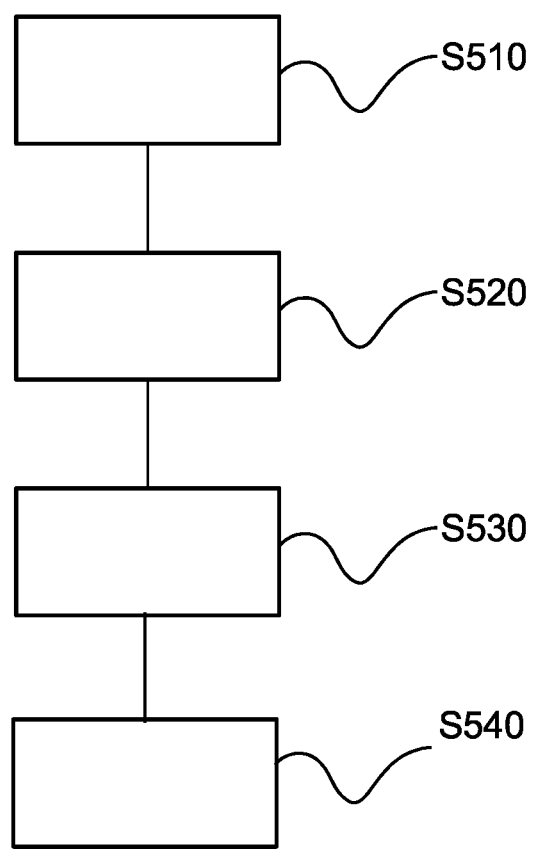
FIG. 5 shows a flow chart of a method to support patient positioning in imaging or radiation therapy.

The coding is agreed on with the patient by prior verbal instruction through a health care worker, by printed-material such as leaflet, or by email. website or any other communication outlet. On the above mentioned display DD for displaying the explanations on what each code means, additional patient specific modification might be included. It will be understood that the haptic signal envisaged herein for patent prepositioning, may be used in addition to communicate information/instruction by coding. In addition, once the patient is correctly positioned, the haptic signal may still be applied from the transmitter TX, but this time solely for communicating information through the coding, not necessarily related to the positioning. Reference is now made to FIG. 5 that shows a flow diagram flow chart of a method to support patient positioning. The method may be used preferably for imaging purposes but may also be used instead in radiation therapy (RT). In other words, the above described embodiments may all be used with a radiation therapy delivery device such as a LINAC or others, where correct positioning of the patient during treatment delivery is important.

Although the below described steps relate to the above described systems FIGS. 1-4 these steps are not necessarily tied to the described system and the below described method for patient's position support may also be understood as a teaching in their own right.

At step S510 a relative distance between a current position of a ROI and a target area is established. The target area may be situated in an examination region of an imaging apparatus or in a treatment area of an RT delivery apparatus. Establishing the distance may be achieved by receiving at a receiver RX equipment, such as sensor, an incoming measurement signal that can be correlated with the current position of patient, or at least with the current position of the ROI.

At step S520 a transmitter is operated to generate an outgoing signal. This outgoing signal is capable of inducing remotely, from a distance, a haptic sensation on the patient's skin, in between or during imaging or RT delivery. The outgoing signal may either act directly on the bare skin of the patient or may act indirectly through an intermediate layer such as a piece of cloth. The transmitter is spatially arranged at or in the imaging apparatus or RT delivery apparatus or is at last arranged in an imaging or treatment room where the patient is located.

At step S530 the outgoing signal is modified so as to nudge the patient in a manner so that the region of interest is being moved towards the target area or, if the region of interest is already in the target area, that it so remains. The modification of the outgoing signal is in dependence on the determined relative distance between a current position of the ROI and the target region inside an examination or treatment region. In particular, the modification of the outgoing ("nudging") signal may include changing a direction of the signal and/or modulating the signal by varying any one or both of intensity or a pulse frequency.

In particular, in an automated setting, the spatial direction of the nudging signal is chosen so that the signal propagates and acts along an imaginary line extending between the current position of the region of interest and the target area. More particularly, the impact region on the patient is so chosen such that the region of interest is situated spatially in between the target area and the impact region.

Any one of a frequency intensity and/or direction may be modified as a function of a current distance of the region of interest, and hence of the patient, to the target area. The distance is a function of a current position of the ROI or patient. Referring back to step S510, the current position may be established by any suitable localization scheme. The current position may be ascertained based on echo location, image data derived from video camera surveillance including an optical light sensor, depth sensing sensor, infrared sensor or a combination or sub-combination of any of the forgoing sensors. In embodiments, the sensing of the current ROI position may be established by operating the imaging apparatus to acquire a scan scout image. A scout image in X-ray imaging, such as in CT, is one where a lower dose is used, compared to diagnostic imaging.

Image processing techniques such as image recognition may be used to isolate in the imagery the region of interest and to correlate this information through a world coordinate system located at the imaging apparatus with the target area.

The modification of the outgoing signal and the determination of the current position of the ROI may be done in closed-loop architecture. In particular, a backscatter or back-reflection of the outgoing nudging signal may be used to establish the current position.

In addition or instead of automatically determining the distance at step S510, the outgoing nudging signal may be modified as described above in response to a user request received through a user interface such as a joy stick operated by the user.

At step S540, which is optional, the outgoing signal or a different signal is modulated so as to act as a respiratory rate control. In this embodiment, a vital sign is received from the patient and a pulse frequency or intensity of the outgoing signal and/or that of a different signal generated elsewhere by a suitable (different) transmitter is controlled in dependence on the measured vital sign signal. In particular, in embodiments the vital sign signal is a heart rate reading from the patient and the outgoing signal or the difference signal is caused to pulse in a frequency less than or above the currently measured heart rate of the patient. This has been shown to act on a calming manner on the patient to reduce breathing respiratory rate RRT. In addition or instead, the outgoing signal is generated out-of phase with the heart rate or other periodic metric derivable from other vital sign measurements, such as a blood pressure monitoring, blood oxidization, etc.

In addition or instead to the above, at a further optional step, the outgoing signal and/or the or a third signal may be operated in a manner to mimic human touching such as patting or tapping the patient. In this embodiment the outgoing signal is pulsed in a rhythmic pattern to simulate human touch action to calm the patient.

In addition or instead to the above, at a further optional step, the outgoing signal may be coded to deliver an instruction/information to the patient other than positioning requests. The coding may include application of specific modulation patterns, such as pulse frequency and/or amplitude that represent a certain agreed instruction/information to be communicated to the patient.

One or more features disclosed herein may be configured or implemented as/with circuitry encoded within a computer-readable medium, and/or combinations thereof. Circuitry may include discrete and/or integrated circuitry, application specific integrated circuitry (ASIC), a system-on-a-chip (SOC), and combinations thereof, a machine, a computer system, a processor and memory, a computer program.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A system, comprising:
   an imaging apparatus or a radiation therapy delivery apparatus;
   at least one transmitter configured to generate from a distance an outgoing signal capable of impacting on a patient's skin, thereby causing a haptic sensation at an impact region on the patient's skin; and
   a control logic circuit configured to modify the outgoing signal based on a distance between i) a current position of a region of interest of the patient and ii) a target area in the imaging apparatus or in the radiation therapy apparatus, wherein the control logic circuit is further configured to receive a measurement signal in relation to the patient and modify the outgoing signal based on the measurement signal, wherein the measurement signal represents a patient's vital sign, and wherein the outgoing signal is capable to urge the patient to move to a position such that the region of interest is or remains within the target area in order to achieve a correct patient positioning in an imaging procedure or radiation therapy.

2. The system of claim 1, wherein the control logic circuit is configured to modify the outgoing signal by i) changing a position of the impact region relative to the region of interest), and/or ii) changing a modulation pattern of the outgoing signal.

3. The system of claim 1, wherein the control logic circuit operates automatically or in response to the input request received through a user interface.

4. The system of claim 3, wherein the user interface allows remote controlling of the control logic circuit.

5. The system of claim 1, comprising a localizer module circuit configured to determine the current position of the region of interest.

6. The system of claim 5, wherein the localizer module circuit is coupled to a receiver configured to sense an incoming signal, wherein the localizer module circuit determines the current position of the region of interest based on the incoming signal.

7. The system of claim 1, wherein the transmitter is configured as at least one of a midair ultrasound haptic transmitter, an air nozzle, the outgoing signal being a jet of air, and an electromagnetic wave transmitter.

8. The system of claim 1, wherein the patient resides in or at the imaging apparatus or resides in or at the radiation therapy delivery apparatus.

9. The system of claim 1, wherein the imaging apparatus is one of an X-ray imaging apparatus, a magnetic resonance imaging apparatus, and a PET/SPECT imaging apparatus.

10. The system of claim 1, wherein the control logic circuit is configured to encode in the outgoing signal information to be communicated to the patient.

11. A computer-implemented method, comprising:
   providing an imaging apparatus or a radiation therapy delivery apparatus;
   generating, from a distance, with at least one transmitter, an outgoing signal capable of impacting on a patient's skin, thereby causing a haptic sensation at an impact region on the patient's skin; and
   modifying, by a control logic circuit, the outgoing signal based on a distance between i) a current position of a region of interest of the patient and ii) a target area in the imaging apparatus or in the radiation therapy apparatus, wherein the control logic circuit is further configured to receive a measurement signal in relation to the patient and modify the outgoing signal based on the measurement signal, wherein the measurement signal represents a patient's vital sign, and wherein the outgoing signal is capable to urge the patient to move to a position such that the region of interest is or remains within the target area in order to achieve a correct patient positioning in an imaging procedure or radiation therapy.

12. A non-transitory computer readable medium for storing executable instructions that, when executed, cause the method of claim 11 to be performed.

* * * * *